US011844946B2

(12) United States Patent
Ironi et al.

(10) Patent No.: US 11,844,946 B2
(45) Date of Patent: *Dec. 19, 2023

(54) APPARATUS AND METHODS FOR IMPROVING SENSORY NERVE SENSITIVITY

(71) Applicant: THERANICA BIO-ELECTRONICS LTD., Netanya (IL)

(72) Inventors: Alon Ironi, Haifa (IL); Lana Volokh, Haifa (IL)

(73) Assignee: THERANICA BIO-ELECTRONICS LTD., Netanya (IL)

( * ) Notice: Subject to any disclaimer, the term of this patent is extended or adjusted under 35 U.S.C. 154(b) by 323 days.

This patent is subject to a terminal disclaimer.

(21) Appl. No.: 17/157,230

(22) Filed: Jan. 25, 2021

(65) Prior Publication Data
US 2021/0244950 A1  Aug. 12, 2021

Related U.S. Application Data

(63) Continuation of application No. 15/761,614, filed as application No. PCT/IL2016/051043 on Sep. 21, 2016, now Pat. No. 10,926,090.
(Continued)

(51) Int. Cl.
*A61N 1/36* (2006.01)
*A61N 1/372* (2006.01)

(52) U.S. Cl.
CPC ..... *A61N 1/36103* (2013.01); *A61N 1/36128* (2013.01); *A61N 1/36132* (2013.01); *A61N 1/36071* (2013.01); *A61N 1/37247* (2013.01)

(58) Field of Classification Search
CPC ............. A61B 5/4836; A61B 5/04001; A61B 2562/227; A61B 5/0004; A61B 5/40;
(Continued)

(56) References Cited

U.S. PATENT DOCUMENTS 6,249,706 B1   6/2001  Sobota et al.
6,273,863 B1   8/2001  Avni et al.
(Continued)

FOREIGN PATENT DOCUMENTS

JP  2003-339885 A  12/2003
JP  2004-283316 A  10/2004
(Continued)

OTHER PUBLICATIONS

An International Search Report and a Written Opinion both dated Dec. 14, 2016, which issued during the prosecution of Applicant's PCT/IL2016/051043.
(Continued)

*Primary Examiner* — Deborah L Malamud
(74) *Attorney, Agent, or Firm* — Sughrue Mion, PLLC

(57) ABSTRACT

Apparatus and methods are described for increasing sensitivity of sensory nerves of a portion of a subject's body. A plurality of electrodes (22) are placed at respective locations upon a surface of the body portion. A computer processor (24) applies sets of electrical stimulation pulses to the respective locations upon the surface, via the electrodes. The computer processor receives respective inputs from the subject, via a user interface (26), each of the inputs corresponding to a respective one of the sets of electrical stimulation pulses, and being indicative of a location at which the subject sensed the set of electrical stimulation pulse as having been applied. In response to the inputs from the subject, the computer processor modulates parameters of the sets of electrical stimulation pulses that are applied to respective locations upon the surface of the body portion. Other applications are also described.

27 Claims, 5 Drawing Sheets

Related U.S. Application Data

(60) Provisional application No. 62/221,146, filed on Sep. 21, 2015.

(58) Field of Classification Search
CPC ......... A61B 5/486; A61B 5/6886; A61B 5/72; A61B 5/7475; A61N 1/0456; A61N 1/36034; A61N 1/3603; A61N 1/0476; A61N 1/36135; A61N 1/36031; A61N 1/36139; A61N 1/08; A61N 1/36125; A61N 1/36132; A61N 1/36185; A61N 1/00; A61N 1/04; A61N 1/36; A61N 1/36128; A61N 1/36146; A61N 1/36189; G06F 19/325

See application file for complete search history.

(56) References Cited

U.S. PATENT DOCUMENTS

| | | | |
|---|---|---|---|
| 6,725,094 | B2 | 4/2004 | Saberski |
| 7,483,751 | B2 | 1/2009 | Greenberg et al. |
| 7,556,038 | B2 | 7/2009 | Kirby et al. |
| 7,771,371 | B2 | 8/2010 | Avni |
| 7,998,092 | B2 | 8/2011 | Avni et al. |
| 8,295,925 | B2 | 10/2012 | Brogan et al. |
| 8,306,624 | B2 | 11/2012 | Gerber et al. |
| 8,660,651 | B2 | 2/2014 | Castel et al. |
| 8,774,925 | B2 | 7/2014 | Yarnitsky |
| 8,880,173 | B2 | 11/2014 | DiUbaldi et al. |
| 2005/0234525 | A1 | 10/2005 | Phillips |
| 2006/0047325 | A1 | 3/2006 | Thimineur et al. |
| 2006/0206163 | A1 | 9/2006 | Wahlstrand et al. |
| 2007/0123952 | A1 | 5/2007 | Strother et al. |
| 2007/0233203 | A1 | 10/2007 | Euliano et al. |
| 2008/0033504 | A1 | 2/2008 | Bertolucci |
| 2008/0167580 | A1 | 7/2008 | Avni et al. |
| 2008/0215119 | A1 | 9/2008 | Woods et al. |
| 2009/0182393 | A1 | 7/2009 | Bachinski |
| 2013/0085551 | A1 | 4/2013 | Bachinski et al. |
| 2013/0158627 | A1 | 6/2013 | Gozani et al. |
| 2013/0236867 | A1 | 9/2013 | Avni et al. |
| 2013/0245486 | A1 | 9/2013 | Simon et al. |
| 2014/0148870 | A1 | 5/2014 | Burnett |
| 2014/0194946 | A1 | 7/2014 | Thomas et al. |
| 2014/0249601 | A1 | 9/2014 | Bachinski et al. |
| 2014/0324120 | A1 | 10/2014 | Bogie et al. |
| 2014/0364920 | A1 | 12/2014 | Doan et al. |
| 2014/0371814 | A1 | 12/2014 | Spizzirri et al. |
| 2015/0165186 | A1 | 6/2015 | Dar et al. |

FOREIGN PATENT DOCUMENTS

| | | |
|---|---|---|
| JP | 2010-057804 A | 3/2010 |
| WO | 01/36051 A2 | 5/2001 |
| WO | 2006/022307 A1 | 3/2006 |
| WO | 2006/029257 A2 | 3/2006 |
| WO | 2009/079270 A1 | 6/2009 |
| WO | 2011/053607 A1 | 5/2011 |
| WO | 2013/134330 A1 | 9/2013 |
| WO | 2015/042365 A1 | 3/2015 |
| WO | 2016025323 A1 | 2/2016 |
| WO | 2016/113661 A1 | 7/2016 |
| WO | 2016/155773 A1 | 10/2016 |

OTHER PUBLICATIONS

Perttunen J, "Foot Loading in Normal and Pathological Walking," Jyväskylä: University of Jyväskylä, 2002, 86 p. (Studies in Sport, Physical Education and Health), 89 pages.

U.S. Appl. No. 62/221,146, filed Sep. 21, 2015.

Invitation to Pay Additional Fees, dated Jul. 30, 2018 from the International Bureau in counterpart international application No. PCT/IB2018/053385.

International Search Report & Written Opinion dated Sep. 25, 2018 from the International Bureau in counterpart International application No. PCT/IB2018/053385.

Communication dated Sep. 18, 2018 from the European Patent Office in counterpart application No. 16737139.2.

Non-Final Office Action issued in U.S. Appl. No. 15/761,614, dated May 1, 2020.

Final Office Action issued in U.S. Appl. No. 15/761,614, dated Aug. 25, 2020.

Non-Final Office Action issued in U.S. Appl. No. 16/614,986, dated Jun. 4, 2021.

Notice of Reasons for Refusal dated Feb. 22, 2022 from the Japanese Patent Office in Application No. 2019-565467.

APPARATUS AND METHODS FOR IMPROVING SENSORY NERVE SENSITIVITY

CROSS-REFERENCE TO RELATED APPLICATIONS

The present application is a continuation of U.S. application Ser. No. 15/761,614, filed Mar. 20, 2018, now U.S. Pat. No. 10,926,090, which is the U.S. national stage of International Application PCT/IL2016/051043, filed Sep. 21, 2016, which claims priority from U.S. Provisional Patent Application No. 62/221,146 to Ironi, filed Sep. 21, 2015, entitled "Interactive training device for improving limb sensation in peripheral sensory neuropathy patients."

The above-referenced provisional application is incorporated herein by reference.

FIELD OF EMBODIMENTS OF THE INVENTION

Some applications of the present invention generally relate to medical apparatus and methods. Specifically, some applications of the present invention relate to apparatus and methods for improving sensory nerve sensitivity.

BACKGROUND

Peripheral sensory neuropathy (PSN) is a relatively common debilitating complication of diabetes and other diseases. As described in an article entitled "Peripheral Neuropathy" (published by National Institutes of Health, Department of Health and Human Services, NIH Publication No. 15-4853, December 2014), an estimated 20 million people in the USA alone suffer from peripheral neuropathy. The condition develops as a result of damage to the peripheral nervous system, and symptoms can range from numbness or tingling, to pricking sensations, muscle weakness, pain, and more. Peripheral nerves send sensory information to the brain and spinal cord, and also carry signals from the brain and spinal cord to the muscles to generate movement. Damage to the peripheral nervous system interferes with these vital connections. Peripheral neuropathy distorts and sometimes interrupts messages between the brain and spinal cord and the rest of the body.

Peripheral neuropathies can be presented in a variety of forms and follow different patterns. Symptoms may be experienced over a period of days, weeks, or years. They can be acute or chronic. In chronic forms, symptoms begin subtly and progress slowly. Some people may have periods of relief followed by relapse. Others may reach a plateau stage where symptoms stay the same for many months or years. Many chronic neuropathies worsen over time.

In diabetic neuropathy, one of the most common forms of peripheral neuropathy, nerve damage occurs in an ascending pattern. The first nerve fibers to deteriorate and lose functionality are the ones that travel the farthest from the brain and the spinal cord; numbness is felt in both feet, followed by a gradual regression up both legs.

Peripheral sensory neuropathy in the feet has the secondary impact of disabling movements associated with the feet, such as walking. The reason is that, in order to properly control the movements through messages carried by the motor nerves, the brain needs sensory feedback, which is sent by the sensory nerves. Without the feedback, movements become very difficult to make, or even impossible.

Electrical nerve stimulation is a treatment method based on delivering series of electrical stimuli to nerves. Various forms of electrical nerve stimulation have been used, among other things, as means of pain treatment, muscle relaxation and more.

Neuroplasticity is the ability of the brain to modify its neural connections such as to adapt to challenges in the environment. Scientists have shown that the brain possesses the ability to modify neural connections to better cope with new circumstances. The adult brain continually generates new nerve cells; a process known as neurogenesis. Neuroplasticity is involved in the development and adaptation of sensory functions. The brain is able to adapt, in response to sensory inputs.

SUMMARY OF EMBODIMENTS

In accordance with some applications of the present invention, apparatus and methods are provided to increase the sensitivity of sensory nerves of a portion of a subject's body. Typically, treatment is applied to an extremity (e.g., a hand or a foot), and/or a limb (e.g., an arm or a leg) of a subject suffering from peripheral sensory neuropathy. By increasing the sensitivity of the sensory nerves of the extremity and/or the limb, the sensitivity of the extremity and/or the limb is restored. Typically, application of the apparatus and methods described herein generates a neuroplastic response by the patient's brain. The location in the brain that interprets sensory inputs from the treated body portion generates new neural networks, such that its interpretative ability improves over time. For some applications, even if (due to the neuropathic disease from which the subject suffers) the peripheral sensory nerve cells continue to degrade, the above-described neuroplastic response of the brain to the treatment compensates at least partially for the degradation of the sensory cells. In this manner, the time period over which the subject has practical sensory capability is at least partially extended, in spite of the progress of the disease.

For some applications, during a treatment session (i.e., a training session) sets of electrical stimulation pulses are applied to a plurality of locations upon a surface of the body portion (e.g., the extremity, or the limb) that is being treated. Typically, a plurality of electrodes are disposed upon a wearable garment that is worn by the subject, and the sets of electrical stimulation pulses are applied via the electrodes. (For example, the wearable garment may include a sock, a glove, a cuff, and/or a patch). Respective inputs are received from the subject, each of the inputs corresponding to a respective one of the sets of electrical stimulation pulses, and being indicative of a location at which the subject sensed the set of electrical stimulation pulse as having been applied. For example, the user may provide the inputs to a computer processor via a user interface, which may include user interface components of a personal computer, a smartphone, and/or a tablet device. In response to the inputs from the subject, parameters of the sets of electrical stimulation pulses that are applied to respective locations upon the surface of the body portion are modulated.

Typically, the parameters of the sets of pulses that are applied at respective locations are modulated such that, over the course of a treatment session, the stimulation that is provided at respective locations moves dynamically toward the sensitivity threshold of the subject. Thus, in response to receiving inputs from the subject that are indicative of the subject having correctly sensed a location at which electrical stimulation pulses were applied, the strength of the stimulation at the location is iteratively reduced, e.g., by reducing the temporal width of the set of electrical stimulation pulses, the frequency of the electrical stimulation pulses, and/or the current intensity of the set of electrical stimulation pulses. Conversely, in response to receiving an input from the subject that is indicative of the subject having sensed a given set of electrical stimulation pulses as having been applied at a location that is different from the location at which the set of electrical stimulation pulses was applied, the strength of the stimulation that is applied to the location is iteratively increased, until an input is received from the subject that is indicative of the subject having correctly sensed a given set of electrical stimulation pulses as having been applied at the location. Similarly, in response to receiving an input from the subject that is indicative of the subject not having sensed electrical stimulation pulses as having been applied at a given location, the strength of the stimulation that is applied to the location is iteratively increased, until an input is received from the subject that is indicative of the subject having correctly sensed a given set of electrical stimulation pulses as having been applied at the location. For some applications, over the course of a treatment session, the strength of the stimulation that is applied to a location increases and decreases (e.g., by increasing and decreasing, in an alternating manner), as the strength of the stimulation that is applied to the location converges toward the subject's sensitivity threshold.

For some applications, outputs are generated to the subject (e.g., via the user interface), in order to elicit a neuroplastic response. For example, during a treatment session, in response to the inputs from the subject, outputs may be generated that are indicative of whether the subject correctly sensed locations at which respective sets of the electrical stimulation pulse were applied. Alternatively or additionally, in response to inputs from the subject over a treatment session, an output may be generated that is indicative of levels of sensitivity of respective locations upon the surface of the body portion, during the previous treatment session. Typically, such outputs are generated upon a graphical representation of the portion of the body that is being treated. For example, a graphical image of a foot or a hand may be displayed with indications of levels of sensitivity of respective locations upon the surface of the foot or the hand displayed upon the image.

For some applications, the following steps are applied in an iterative manner. Sets of electrical stimulation pulses are applied simultaneously to the surface of the body portion, via a given pair of electrodes, the electrodes being separated from each other by a given distance. The computer processor receives an input from the subject that is indicative of whether the subject sensed the sets of electrical stimulation pulses as coming from a single location, or more than one location. In response to the input from the subject, the computer processor designates another pair of electrodes via which to simultaneously apply sets of electrical stimulation pulses to the surface of the body portion, the other pair of electrodes being separated from each other by a distance that is different from the given distance. Sets of electrical stimulation pulses are then applied to the surface of the body portion, via the other pair of electrodes. Typically, the distance between the selected electrode pairs is modulated such that, over the course of a treatment session, the stimulation that is provided at respective regions of the surface of the body portion moves dynamically toward the two-point sensitivity threshold of the subject at the respective regions. Thus, in response to the subject having correctly sensed the sets of electrical stimulation pulses as having been applied to more than one location, a pair of electrodes that are closer to one another are chosen as the next pair of electrodes, and in response to the subject having sensed the sets of electrical stimulation pulses as having been applied to a single location, a pair of electrodes that are farther apart from one another are chosen as the next pair of electrodes. For some applications, over the course of a treatment session, within a given region, the distance between electrodes, via which simultaneous stimulation is applied, increases and decreases (e.g., by increasing and decreasing, in an alternating manner), as the distance between electrodes via which simultaneous stimulation is applied converges toward the subject's two-point sensitivity threshold.

There is therefore provided, in accordance with some applications of the present invention, apparatus for increasing sensitivity of sensory nerves of a portion of a body of a subject, the apparatus including:

a plurality of electrodes configured to be placed at respective locations upon a surface of the body portion;

a user interface; and at least one computer processor configured to:

apply sets of electrical stimulation pulses to the respective locations upon the surface of the body portion, via the electrodes, receive respective inputs from the subject, via the user interface, each of the inputs corresponding to a respective one of the sets of electrical stimulation pulses, and being indicative of a location at which the subject sensed the set of electrical stimulation pulse as having been applied, and in response to the inputs from the subject, modulate parameters of the sets of electrical stimulation pulses that are applied to respective locations upon the surface of the body portion.

In some applications, the computer processor is configured to:

apply the sets of electrical stimulation pulses to the plurality of locations upon the surface of the body portion by applying to at least some of the plurality of locations, sets of electrical stimulation pulses that are configured to generate muscle movement within the body portion, and receive the inputs from the subject by receiving at least some inputs from the subject that are indicative of locations at which the subject sensed the muscle movement.

In some applications, the computer processor is configured:

to receive surface electromyography signals from the respective locations upon the surface of the body portion, and to modulate parameters of the sets of electrical stimulation pulses that are applied to respective locations upon the surface of the body portion by modulating parameters of the sets of electrical stimulation pulses that are applied to respective locations upon the surface of the body portion in response to the inputs from the subject and the detected surface electromyography signals.

In some applications, in response to the inputs from the subject, the computer processor is configured to generate outputs to the subject, via the user interface, that are indicative of whether the subject correctly sensed locations at which respective sets of the electrical stimulation pulse were applied.

In some applications, the computer processor is configured to dynamically modulate parameters of the sets of electrical stimulation pulses that are applied to respective locations upon the surface of the body portion, while continuing to apply sets of electrical stimulation pulses to the plurality of locations upon the surface of the body portion.

In some applications, in response to inputs from the subject over a course of a treatment session, the computer processor is configured to generate an output, via the user interface, that is indicative of levels of sensitivity of respective locations upon the surface of the body portion.

In some applications, the computer processor is configured to modulate parameters of the sets of electrical stimulation pulses that are applied to respective locations upon the surface of the body portion by modulating parameters of the sets of pulses that are applied at the respective locations, over a course of a treatment session, such that stimulation that is provided at the respective locations moves dynamically toward a sensitivity threshold of the subject.

In some applications, the computer processor is configured to modulate parameters of the sets of electrical stimulation pulses that are applied to respective locations upon the surface of the body portion by, during the treatment session, both increasing and decreasing a strength of stimulation that is provided at a given location, as the strength of the stimulation that is applied to the given location converges toward the subject's sensitivity threshold at the given location.

In some applications, the computer processor is configured to modulate parameters of the sets of electrical stimulation pulses that are applied to respective locations upon the surface of the body portion by:

in response to receiving an input from the subject that is indicative of the subject having correctly sensed a location at which a given set of electrical stimulation pulses were applied, reducing at least one parameter of a further set of electrical stimulation pulses that is applied to the location, the at least one parameter being selected from the group consisting of: a temporal width of the set of electrical stimulation pulses, a frequency of the electrical stimulation pulses, and a current intensity of the electrical stimulation pulses.

In some applications, the computer processor is configured to modulate parameters of further sets of electrical stimulation pulses that are applied to the location by, iteratively, reducing the selected at least one parameter of sets of electrical stimulation pulses that are applied to the location, in response to receiving inputs from the subject that are indicative of the subject having correctly sensed the location at which the sets of electrical stimulation pulses were applied.

In some applications, the computer processor is configured to modulate parameters of the sets of electrical stimulation pulses that are applied to respective locations upon the surface of the body portion by:

in response to receiving an input from the subject that is indicative of the subject having sensed a given set of electrical stimulation pulses as having been applied at a location that is different from the location at which the set of electrical stimulation pulses was applied, increasing at least one parameter of a further set of electrical stimulation pulses that is applied to the location at which the set of electrical stimulation pulses was applied, the at least one parameter being selected from the group consisting of: a temporal width of the set of electrical stimulation pulses, a frequency of the electrical stimulation pulses, and a current intensity of the electrical stimulation pulses.

In some applications, the computer processor is configured to modulate parameters of further sets of electrical stimulation pulses that are applied to the location by, iteratively, increasing the selected at least one parameter of further sets of electrical stimulation pulses that are applied to the location at which the set of electrical stimulation pulses was applied, until an input is received from the subject that is indicative of the subject having correctly sensed a given set of electrical stimulation pulses as having been applied at the location.

In some applications, the computer processor is configured to modulate parameters of the sets of electrical stimulation pulses that are applied to respective locations upon the surface of the body portion by:

in response to receiving an input from the subject that is indicative of the subject not having sensed electrical stimulation pulses as having been applied at a given location, increasing at least one parameter of a further set of electrical stimulation pulses that is applied to the given location, the at least one parameter being selected from the group consisting of: a temporal width of the set of electrical stimulation pulses, a frequency of the electrical stimulation pulses, and a current intensity of the electrical stimulation pulses.

In some applications, the computer processor is configured to modulate parameters of the sets of further sets of electrical stimulation pulses that are applied to respective locations upon the surface of the body portion by, iteratively, increasing the selected at least one parameter of sets of electrical stimulation pulses that are applied to the given location, until an input is received from the subject that is indicative of the subject having correctly sensed a given set of electrical stimulation pulses as having been applied at the given location.

In some applications, the user interface includes user interface components of one or more devices selected from the group consisting of: a personal computer, a smartphone, and a tablet device.

In some applications, the at least one computer processor includes a computer processor of the selected one or more devices.

In some applications, the apparatus further includes a wearable garment configured to be worn by the subject, and the plurality of electrodes are disposed upon the wearable garment and are configured to be placed at the respective locations upon the surface of the body portion by the subject wearing the garment.

In some applications, the garment is selected from the group consisting of: a glove, a sock, a patch, and a cuff.

There is further provided, in accordance with some applications of the present invention, a method including:

increasing sensitivity of sensory nerves of a portion of a body of a subject, by:
  applying sets of electrical stimulation pulses to a plurality of locations upon a surface of the body portion;
  receiving respective inputs from the subject, each of the inputs corresponding to a respective one of the sets of electrical stimulation pulses, and being indicative of a location at which the subject sensed the set of electrical stimulation pulse as having been applied; and
  in response to the inputs from the subject, modulating parameters of the sets of electrical stimulation pulses that are applied to respective locations upon the surface of the body portion.

There is further provided, in accordance with some applications of the present invention, a method including:

increasing sensitivity of sensory nerves of a portion of a body of a subject, by, iteratively:

simultaneously applying sets of electrical stimulation pulses to two locations upon a surface of the body portion, the two locations being separated from each other by a given distance;

receiving an input from the subject that is indicative of whether the subject sensed the sets of electrical stimulation pulses as having been applied to a single location or more than one location;

in response to the input from the subject, designating another set of two locations upon the surface of the body portion at which to simultaneously apply sets of electrical stimulation pulses, the two locations being separated from each other by a distance that is different from the given distance; and simultaneously applying sets of electrical stimulation pulses to the other set of at least two locations upon the surface of the body portion.

There is further provided, in accordance with some applications of the present invention, apparatus for increasing sensitivity of sensory nerves of a portion of a body of a subject, the apparatus including:

a plurality of electrodes configured to be placed at respective locations upon a surface of the body portion;

a user interface; and at least one computer processor configured to, iteratively:

simultaneously apply sets of electrical stimulation pulses to the surface of the body portion, via a given pair of electrodes, the pair of electrodes being separated from each other by a given distance, receive an input from the subject that is indicative of whether the subject sensed the sets of electrical stimulation pulses as having been applied to a single location, or more than one location, in response to the input from the subject, designate another pair of electrodes via which to simultaneously apply sets of electrical stimulation pulses to the surface of the body portion, the other pair of electrodes being separated from each other by a distance that is different from the given distance, and simultaneously apply sets of electrical stimulation pulses to the surface of the body portion, via the other pair of electrodes.

In some applications, the computer processor is configured to designate the other pair of electrodes by, in response to the subject having correctly sensed the sets of electrical stimulation pulses as having been applied to more than one location, designating another pair of electrodes, the other pair of electrodes being separated from each other by a distance that is less than the given distance.

In some applications, the computer processor is configured to designate the other pair of electrodes by, in response to the subject having sensed the sets of electrical stimulation pulses as having been applied to a single location, designating another pair of electrodes, the other pair of electrodes being separated from each other by a distance that is greater than the given distance.

In some applications, in response to the input from the subject, the computer processor is configured to generate an output, via the user interface, that is indicative of whether the subject correctly sensed the sets of electrical stimulation pulses as having been applied to more than one location.

In some applications, in response to inputs from the subject over a course of a treatment session, the computer processor is configured to generate an output, via the user interface, that is indicative of levels of sensitivity of respective locations upon the surface of the body portion.

In some applications, the computer processor is configured to designate the other pair of electrodes by, at respective regions of the surface of the body portion, designating electrodes via which to simultaneously apply sets of electrical stimulation pulses, such that, over a course of a treatment session, the distances between the electrodes move dynamically toward a two-point sensitivity threshold of the subject at the respective regions.

In some applications, the computer processor is configured to designate the other pair of electrodes by, within a given region of the surface of the body portion, designating electrodes via which to simultaneously apply sets of electrical stimulation pulses, such that, over the course of the treatment session, distances between the electrodes both increase and decrease, as the distances between the electrodes that are designated converge toward the subject's two-point sensitivity threshold at the region.

In some applications, the apparatus further includes a wearable garment configured to be worn by the subject, the plurality of electrodes are disposed upon the wearable garment and are configured to be placed at the respective locations upon the surface of the body portion by the subject wearing the garment.

In some applications, the garment is selected from the group consisting of: a glove, a sock, a patch, and a cuff.

In some applications, the user interface includes user interface components of one or more devices selected from the group consisting of: a personal computer, a smartphone, and a tablet device.

In some applications, the at least one computer processor includes a computer processor of the selected one or more devices.

The present invention will be more fully understood from the following detailed description of embodiments thereof, taken together with the drawings, in which:

DETAILED DESCRIPTION OF EMBODIMENTS

Figure 1:
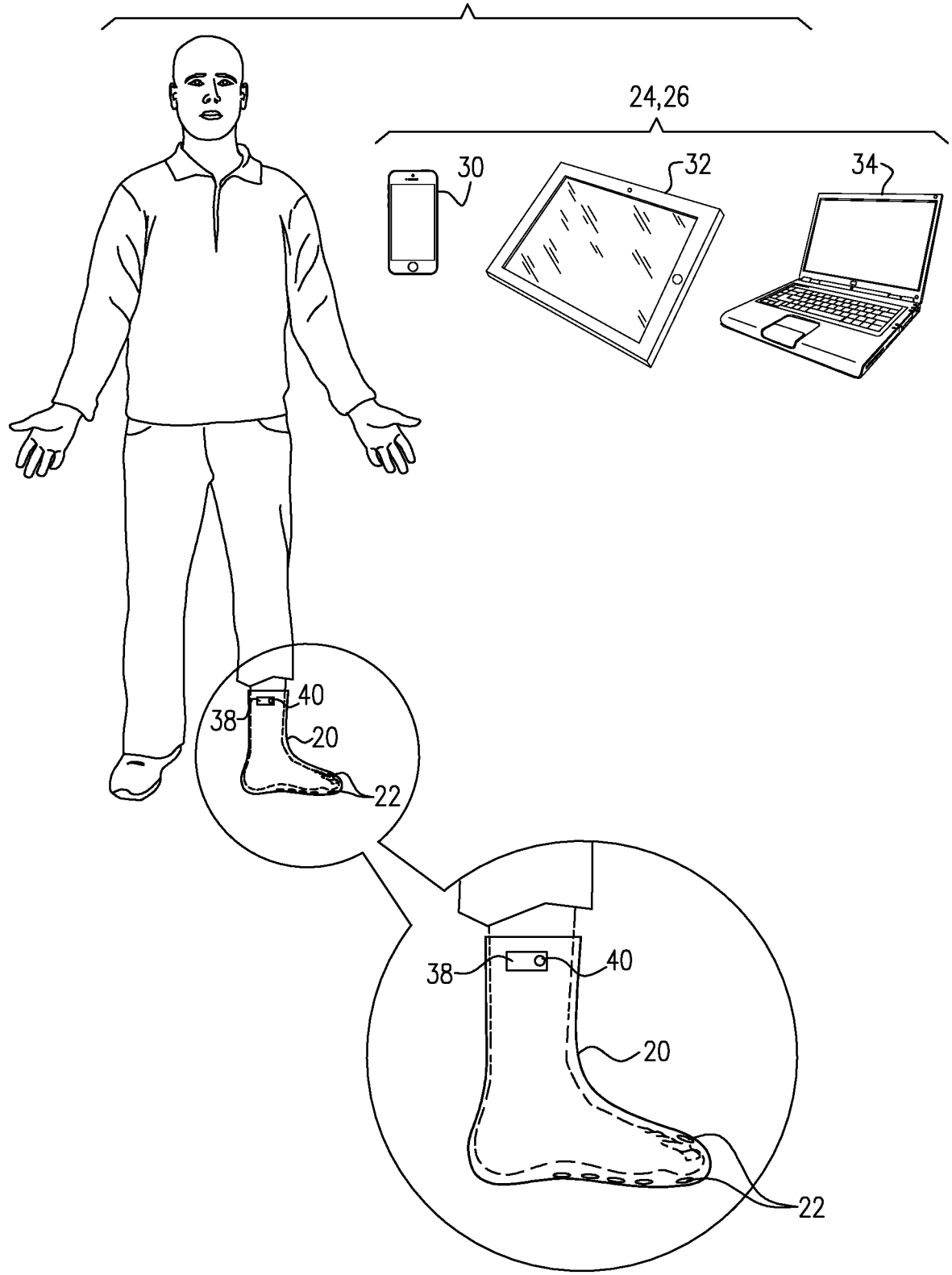
FIG. 1 is a schematic illustration of a garment having electrodes disposed thereon, a computer processor, and a user interface, in accordance with some applications of the present invention.

Reference is now made to FIG. 1, which is a schematic illustration of a garment 20 having electrodes 22 disposed thereon, a computer processor 24 and a user interface 26, in accordance with some applications of the present invention.

As shown in FIG. 1, garment 20 is a sock. However, the scope of the present invention includes any garment that can be worn by a subject, including but not limited to, a glove, a cuff, and a wearable patch. Typically, a treatment is applied to an extremity (e.g., a hand or a foot), and/or a limb (e.g., an arm or a leg) of a subject suffering from peripheral sensory neuropathy. By increasing the sensitivity of the sensory nerves of the extremity and/or the limb, the sensitivity of the extremity and/or the limb is restored. Garment 20 is typically a garment that is suitable for being placed upon the extremity and/or the limb that is being treated. For example, a sock is typically used for treating a foot, a glove is typically used for treating a hand, and a cuff or a patch is typically used for treating an arm or a leg. Garment 20 is typically sized such as to fit the subject.

For some applications, user interface 26 includes user interface components of one or more devices, such as a smartphone 30, a tablet device 32, and/or a personal computer 34. Typically, for such applications, computer processor 24 is the computer processor of the device. For some applications, an electronic module 38 is couplable to the garment and contains circuitry that is configured to communicate with the electrodes. For some applications, the electronic module performs some of the computer processor functionalities that are described herein. Alternatively or additionally, the electronic module is used to facilitate communication between a computer processor of an external device (such as smartphone 30, tablet device 32, and/or personal computer 34) and the electrodes, typically using known protocols, such as Wifi, Bluetooth®, ZigBee®, or any near field communication (NFC) protocol. Typically, the electronic module can be removed from the garment, for example, to replace the battery, to clean the garment, etc. For some applications, the electronic module includes an accessible button 40, which allows the user to turn the electrode-supporting garment on and off.

Typically, an array of electrodes 22 is disposed upon the garment. Typically, at least some of electrodes 22 are configured as stimulating electrodes, as described in further detail hereinbelow. For example, the array may include more than 10 and/or less than 40 (e.g., 10-40) stimulating electrodes. For some applications, the stimulating electrodes are configured to be paired with one another. For some applications, at least some of the electrodes act as sensing electrodes. For example, some of the electrodes may be configured to perform surface electromyography sensing, as described in further detail hereinbelow.

Figure 2:
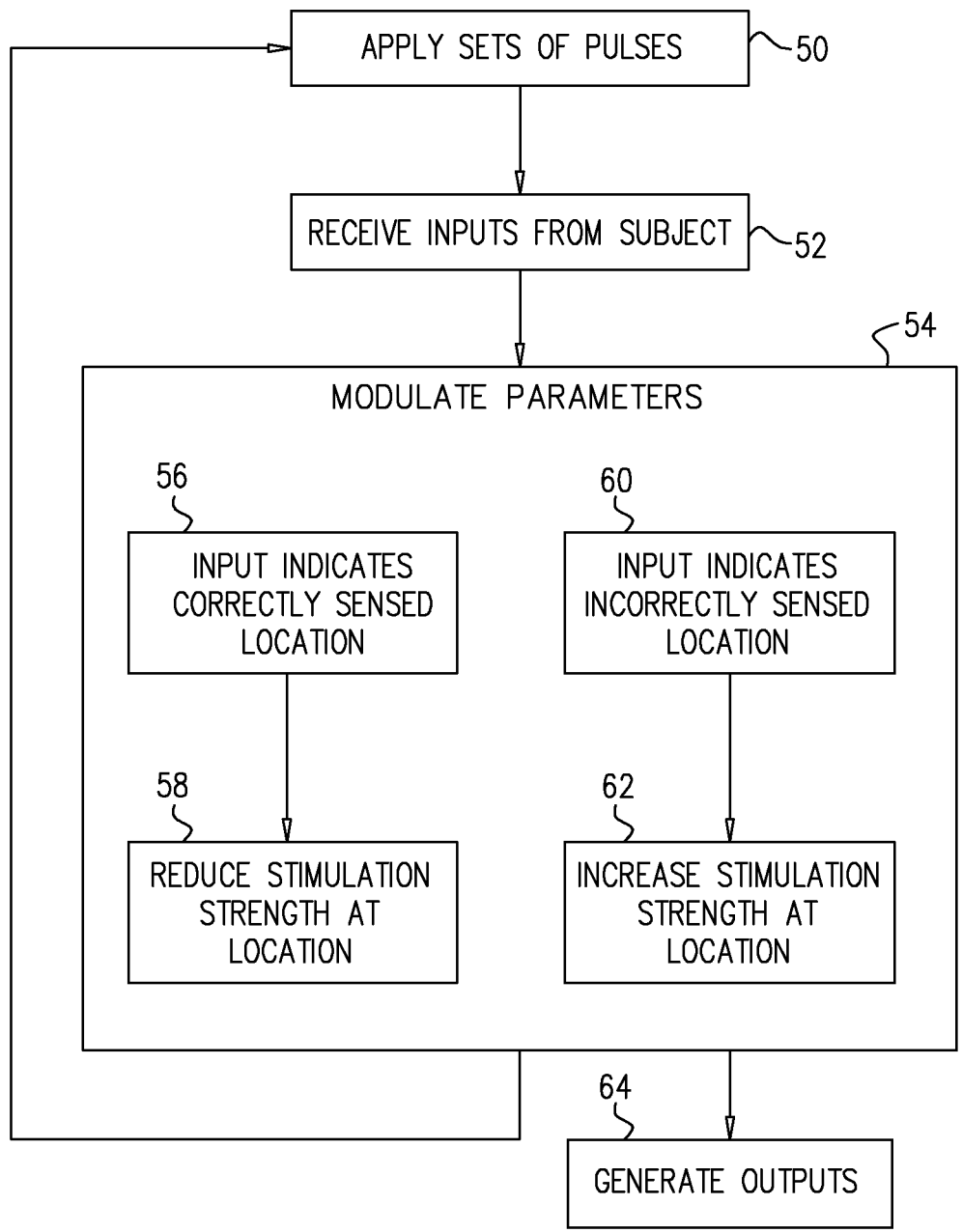
FIG. 2 is a flowchart showing steps of a method that is performed, in accordance with some applications of the present invention.

Reference is now made to FIG. 2, which is a flowchart showing steps of a method that is performed during a treatment session (i.e., a training session), in accordance with some applications of the present invention. Typically, the subject uses the device a few times a week (e.g., 3-7 times a week), with each treatment session typically lasting between 10 minutes and one hour (e.g., approximately 20 minutes). At the beginning of each session, the user typically turns on each electrode-supporting garment 20, e.g., via button 40, and activates user interface 26, typically, by opening a program or application that is run on the computer processor (e.g., a program or application that is run on smartphone 30, tablet device 32, and/or personal computer 34). Typically, the program or application connects electronically with the electrode-supporting garment (e.g., using a communication protocol as described hereinabove), with the program or application being the "master" and the electrode-supporting garment(s) being the "slave(s)." For some applications, a graphical representation of the portion of the body that is being treated is displayed upon the user interface, as described in further detail hereinbelow with reference to FIG. 5. For example, a graphical image of a foot or a hand may be displayed. For some applications, outputs are displayed upon the graphical representation of the portion of the subject's body that is being treated, as described in further detail hereinbelow.

In a first step 50 of the training method, computer processor 24 applies sets of electrical stimulation pulses to a plurality of locations upon a surface of the body portion (e.g., the extremity or the limb) that is being treated. Typically, the sets of electrical stimulation pulses are applied via electrodes 22, which are disposed on garment 20.

In a second step 52, respective inputs are received from the subject, each of the inputs corresponding to a respective one of the sets of electrical stimulation pulses, and being indicative of a location at which the subject sensed the set of electrical stimulation pulse as having been applied. Typically, the user provides the inputs to computer processor 24 via user interface 26. As described hereinabove, for some applications, a graphical representation of the portion of the body that is being treated is displayed upon the user interface. For some applications, the user indicates the location at which he/she sensed a given set of electrical stimulation pulses as having been applied, by indicating the location upon the displayed graphical representation of the body portion.

In a third step 54, in response to the inputs from the subject, parameters of the sets of electrical stimulation pulses that are applied to respective locations upon the surface of the body portion are modulated. Typically, the parameters of the sets of pulses that are applied at respective locations are modulated such that, over the course of a treatment session, the stimulation that is provided at respective locations moves dynamically toward the sensitivity threshold of the subject. Thus, in response to receiving inputs from the subject that are indicative of the subject having correctly sensed a location at which electrical stimulation pulses were applied (sub-step 56), the strength of the stimulation at the location is iteratively reduced, e.g., by reducing the temporal width of the set of electrical stimulation pulses, the frequency of the electrical stimulation pulses, and/or the current intensity of the set of electrical stimulation pulses (sub-step 58). Conversely, in response to receiving an input from the subject that is indicative of the subject having sensed a given set of electrical stimulation pulses as having been applied at a location that is different from the location at which the set of electrical stimulation pulses was applied (sub-step 60), the strength of the stimulation that is applied to the location is iteratively increased (sub-step 62), until an input is received from the subject that is indicative of the subject having correctly sensed a given set of stimulation pulses as having been applied at the location. Similarly, in response to receiving an input from the subject that is indicative of the subject not having sensed electrical stimulation pulses as having been applied at a given location (sub-step 60), the strength of the stimulation that is applied to the location is iteratively increased (sub-step 62), until an input is received from the subject that is indicative of the subject having correctly sensed a given set of electrical stimulation pulses as having been applied at the location.

For some applications, over the course of a treatment session, the strength of the stimulation that is applied to a location increases and decreases (e.g., by increasing and decreasing, in an alternating manner), as the strength of the stimulation that is applied to the location converges toward the subject's sensitivity threshold.

For some applications, the sets of electrical stimulation pulses that are applied at at least some locations are configured to generate muscle movement within the body portion. Typically, for such applications, the inputs that are received from the subject are indicative of locations at which the subject sensed the muscle movement.

For some applications, in a fourth step 64, outputs are generated to the subject (e.g., via user interface 26), in order to elicit a neuroplastic response. For example, during the treatment session, in response to the inputs from the subject, outputs may be generated that are indicative of whether the subject correctly sensed locations at which respective sets of the electrical stimulation pulses were applied. For some applications, such outputs are generated upon a graphical representation of the portion of the body that is being treated, e.g., as described hereinbelow with reference to FIG. 5.

Figure 3:
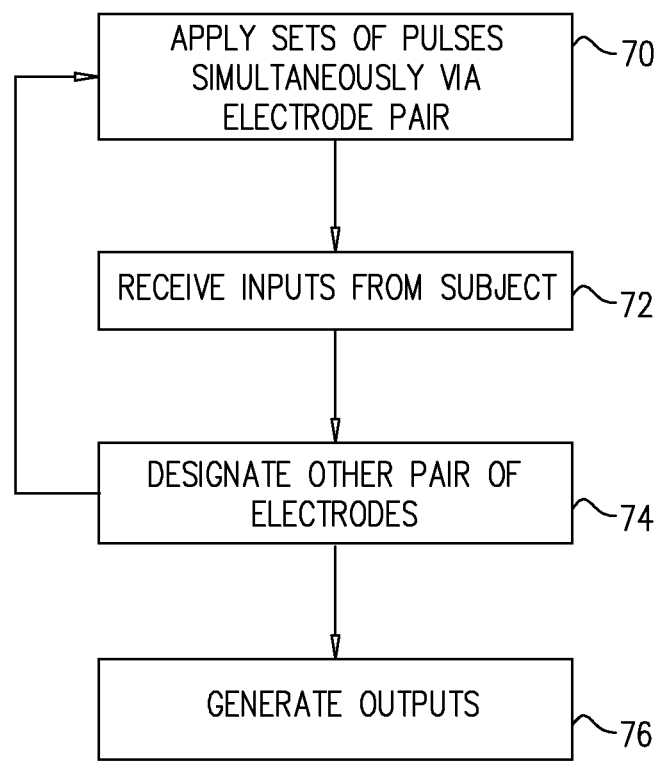
FIG. 3 is a schematic illustration of a flowchart showing steps of an alternative or additional method that is performed, in accordance with some applications of the present invention.

FIG. 3 is a schematic illustration of a flowchart showing steps of another method that is performed in accordance with some applications of the present invention. The preliminary steps of this method (e.g., switching on the electrode-supporting garment, and an application or program on the user interface) are typically as described hereinabove with reference to FIG. 2. The following steps are typically then performed in an iterative manner.

In a first step 70, the computer processor applies sets of electrical stimulation pulses simultaneously to the surface of the body portion, via a given pair of electrodes, the electrodes being separated from each other by a given distance.

In a second step 72, the computer processor receives one or more inputs from the subject that is indicative of whether the subject sensed the sets of electrical stimulation pulses as coming from a single location, or more than one location.

In a third step 74, in response to the input from the subject, the computer processor designates another pair of electrodes via which to simultaneously apply sets of electrical stimulation pulses to the surface of the body portion, the other pair of electrodes being separated from each other by a distance that is different from the given distance. Sets of electrical stimulation pulses are then applied to the surface of the body portion, via the other pair of electrodes. Typically, the distance between the selected electrode pairs is modulated such that, over the course of a treatment session, the stimulation that is provided at respective regions of the surface of the body portion moves dynamically toward the two-point sensitivity threshold of the subject at the respective regions. Typically, in response to the subject having correctly sensed the sets of electrical stimulation pulses as having been applied to more than one location, a pair of electrodes that are closer to one another are chosen as the next pair of electrodes, and in response to the subject having sensed the sets of electrical stimulation pulses as having been applied to a single location, a pair of electrodes that are farther apart from one another are chosen as the next pair of electrodes. For some applications, over the course of a treatment session, within a given region, the distance between electrodes, via which simultaneous stimulation is applied, increases and decreases (e.g., by increasing and decreasing, in an alternating manner), as the distance between electrodes via which simultaneous stimulation is applied converges toward the subject's two-point sensitivity threshold.

For some applications, in a fourth step 76, outputs are generated to the subject (e.g., via user interface 26), in order to elicit a neuroplastic response. For example, during the treatment session, in response to the inputs from the subject, outputs may be generated that are indicative of whether the subject correctly sensed whether electrical stimulation pulses were being applied at one or two locations, at a given region of the surface of the body portion. For some applications, such outputs are generated upon a graphical representation of the portion of the body that is being treated, e.g., as described hereinbelow with reference to FIG. 5.

As described hereinabove, for some applications, at least some of electrodes 22 act as sensing electrodes. For example, some of the electrodes may be configured to perform surface electromyography sensing. For some applications, surface electromyography data are provided to the computer processor, and the computer processor modulates parameters of the electrical stimulation pulses that are applied at respective locations in response to the surface electromyography data. For example, the computer processor may modulate parameters of the electrical stimulation pulses that are applied at respective locations in response to the surface electromyography data, in addition to the inputs from the subject. Or, the computer processor may modulate parameters of the electrical stimulation pulses that are applied at respective locations in response to the surface electromyography data, instead of modulating the parameters of the electrical stimulation pulses in response to the inputs from the subject.

Typically, a treatment session (e.g., a session in which the steps described with reference to FIG. 2 is performed, and/or a session in which the steps described with reference to FIG. 3 is performed) is complete after a pre-defined number of pulses (e.g., between 100 and 500 pulses) has been applied to each location. For some applications, at the end of a treatment session, in response to inputs from the subject over the treatment session, an output is generated that is indicative of levels of sensitivity of respective locations upon the surface of the body portion. For some applications, such outputs are generated upon a graphical representation of the portion of the body that is being treated, e.g., as described hereinbelow with reference to FIG. 5.

Typically, the program or application that is run by the computer processor gradually learns the specific sensory performance of the subject, and locations or regions at which the subject has lower sensitivity (e.g., lower two-point sensitivity) are stimulated more frequently and/or with higher intensity than locations or regions at which the subject has greater sensitivity. From one session to the next, the application or program continues to learn the specific performance of the subject, such that it gradually adapts and fine-tunes the distribution of the pulses across the different locations, as well as the pulse intensity of at each location, based upon the subject's performance. Typically, as the sensory performance of the subject improves, the level of "difficulty" of the application gets greater (by applying less intense stimulations), and vice versa.

Figure 4A:
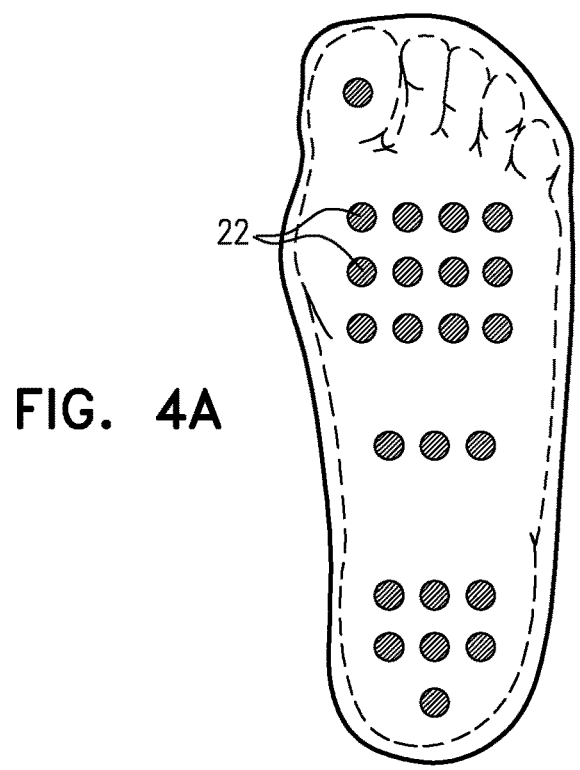
FIGS. 4A and 4B are schematic illustrations of electrode arrays disposed on a wearable garment, in accordance with some applications of the present invention.
Figure 4B:
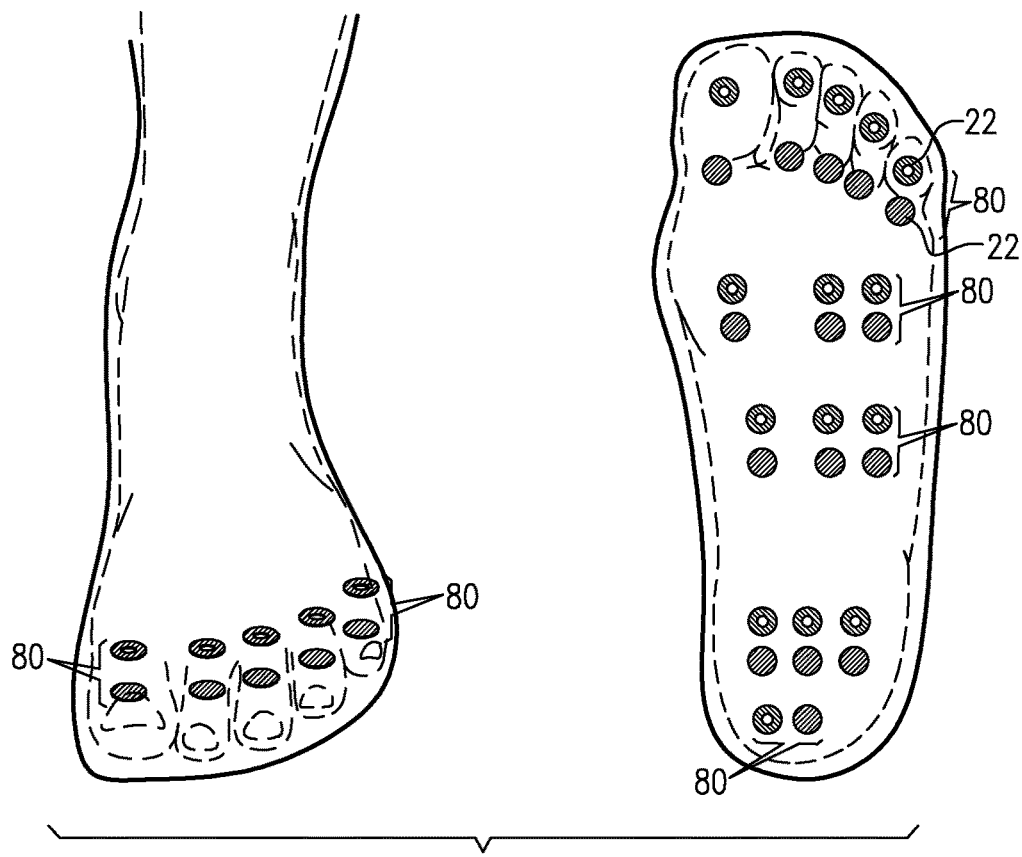

Reference is now made to FIGS. 4A and 4B, which are schematic illustrations of arrays of electrodes 22, in accordance with some applications of the present invention. Typically, the electrodes are disposed upon garment 20. As described hereinabove, typically, at least some of electrodes 22 are configured as stimulating electrodes. For example, the array may include more than 10 and/or less than 40 (e.g., 10-40) stimulating electrodes. For some applications, the stimulating electrodes are configured to be paired with one another into pairs 80, as shown in FIG. 4B. Typically such a configuration is used to perform the method described with reference to FIG. 3. Alternatively, electrode pairs are dynamically configurable from electrodes in an array such as the array shown in FIG. 4A. For some applications, at least some of the electrodes act as sensing electrodes. For example, some of the electrodes may be configured to perform surface electromyography sensing, as described in further detail hereinbelow.

In the example shown in FIGS. 4A and 4B, the electrodes are configured for placement on the subject's foot, and, as such, are typically disposed upon a sock. However, the scope of the present invention includes placing the electrodes on any portion of the subject's body, and using any garment that can be worn by a subject, including but not limited to, a glove, a cuff, and a wearable patch.

Figure 5:
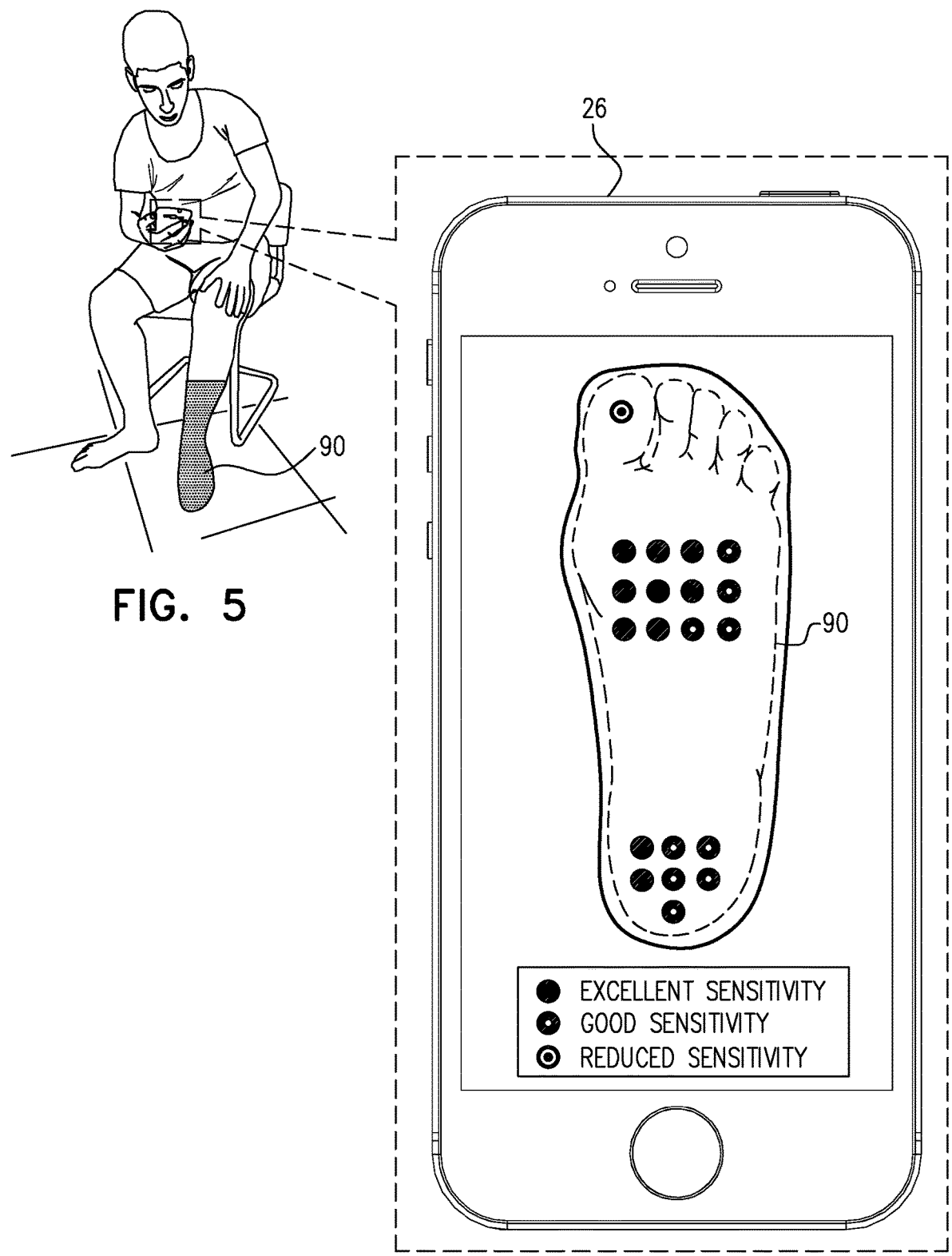
FIG. 5 is a schematic illustration of an example of an output that is generated by a computer processor upon a user interface, in accordance with some applications of the present invention.

Reference is now made to FIG. 5 is a schematic illustration of an example of an output that is generated by computer processor 24 on user interface 26, in accordance with some applications of the present invention. As described hereinabove, for some applications, a graphical representation 90 of the portion of the body that is being treated is displayed upon the user interface. For example, a graphical image of a foot may be displayed, as shown in FIG. 5. Alternatively, a graphical representation of a hand, an arm, a leg, and/or another body portion may be displayed.

For some applications outputs are displayed upon the graphical representation of the portion of the subject's body that is being treated. For example, during the treatment session, outputs may be displayed to the subject that are indicative of the subject's current performance. For some applications, at the end of a treatment session, in response to inputs from the subject over the treatment session, an output is generated that is indicative of levels of sensitivity of respective locations upon the surface of the body portion, as shown in FIG. 5. For some applications, over a plurality of treatment sessions, the application or program records and analyzes the sensory performance of the subject, and it generates personalized sensory maps for each treated body portion. These maps typically present the up to date levels of sensitivity for each location upon the body portion, as well as incremental changes for any selected treatment period.

Typically, the treatments described herein are performed in a recurrent manner. For some applications, the computer processor (via the application or program that is run on the processor) monitors treatments, and, for example, may remind the subject if a given location or body portion has not been treated for a given period of time. For some applications, usage and/or diagnostic information is shared with a physician and/or an insurance company for the purposes of additional monitoring, insurance, etc.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 24. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 24) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk. C++ or the like and conventional procedural programming languages, such as the C programming language or similar programming languages.

It will be understood that blocks of the flowchart shown in FIGS. 2 and 3, and combinations of blocks in the flowcharts, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 24) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 24 and the other computer processors described herein are typically hardware devices programmed with computer program instructions to produce a special purpose computer. For example, when programmed to perform the algorithms described with reference to FIGS. 2 and 3, the computer processor typically acts as a special purpose sensitivity-training computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for increasing sensitivity of sensory nerves of a portion of a body of a subject, the apparatus comprising:
    a plurality of electrodes configured to be placed at respective locations upon a surface of the body portion;
    a user interface; and
    at least one computer processor configured to:
        apply sets of electrical stimulation pulses to the respective locations upon the surface of the body portion, via the electrodes,
        receive respective inputs from the subject, via the user interface, each of the inputs corresponding to a respective one of the sets of electrical stimulation pulses, and being indicative of a location at which the subject sensed the set of electrical stimulation pulses as having been applied, and
        in response to the inputs from the subject and whether the subject (a) correctly sensed a location at which a given set of electrical stimulation pulses were applied or (b) incorrectly sensed that the given set of electrical stimulation pulses were applied at a location different from the location at which the given set of electrical stimulation pulses were applied, modulate at least one parameter of a further set of electrical stimulation pulses that are applied to the location upon the surface of the body portion.

2. The apparatus according to claim 1, wherein the computer processor is configured to:
    apply the sets of electrical stimulation pulses to the plurality of locations upon the surface of the body portion by applying to at least some of the plurality of locations, sets of electrical stimulation pulses that are configured to generate muscle movement within the body portion, and
    receive the inputs from the subject by receiving at least some inputs from the subject that are indicative of locations at which the subject sensed the muscle movement.

3. The apparatus according to claim 1, wherein the computer processor is configured:
    to receive surface electromyography signals from the respective locations upon the surface of the body portion, and
    to modulate parameters of the sets of electrical stimulation pulses that are applied to respective locations upon the surface of the body portion by modulating parameters of the sets of electrical stimulation pulses that are applied to respective locations upon the surface of the body portion in response to the inputs from the subject and the received surface electromyography signals.

4. The apparatus according to claim 1, wherein the computer processor is configured, in response to the inputs from the subject and whether the subject correctly or incorrectly sensed the location at which the given set of electrical stimulation pulses were applied, to generate an output to the subject, via the user interface, that is indicative of whether the subject correctly sensed the location at which the given set of electrical stimulation pulses were applied.

5. The apparatus according to claim 4, wherein the computer processor is configured to generate the output to the subject, via the user interface, upon a graphical representation of the body portion displayed by the user interface.

6. The apparatus according to claim 5, wherein the computer processor is configured to receive each of the inputs indicative of the location at which the subject sensed the set of electrical stimulation pulse as having been applied by receiving an indication from the subject of the location upon the displayed graphical representation of the body portion.

7. The apparatus according to claim 1, wherein the computer processor is configured to dynamically modulate parameters of the sets of electrical stimulation pulses that are applied to respective locations upon the surface of the body portion, while continuing to apply sets of electrical stimulation pulses to the plurality of locations upon the surface of the body portion.

8. The apparatus according to claim 1, wherein the computer processor is configured, in response to the inputs from the subject over a course of a treatment session, to generate an output, via the user interface, that is indicative of levels of sensitivity of respective locations upon the surface of the body portion.

9. The apparatus according to claim 1, wherein the computer processor is configured to modulate parameters of the sets of electrical stimulation pulses that are applied to respective locations upon the surface of the body portion by modulating parameters of the sets of pulses that are applied at the respective locations, over a course of a treatment session, such that stimulation that is provided at the respective locations moves dynamically toward a sensitivity threshold of the subject.

10. The apparatus according to claim 9, wherein the computer processor is configured to modulate parameters of the sets of electrical stimulation pulses that are applied to respective locations upon the surface of the body portion by, during the treatment session, both increasing and decreasing a strength of stimulation that is provided at a given location, as the strength of the stimulation that is applied to the given location converges toward the subject's sensitivity threshold at the given location.

11. The apparatus according to claim 1, wherein the computer processor is configured to modulate parameters of the sets of electrical stimulation pulses that are applied to respective locations upon the surface of the body portion by:
    in response to receiving an input from the subject that is indicative of the subject having correctly sensed the location at which the given set of electrical stimulation pulses were applied, reducing the at least one parameter of the further set of electrical stimulation pulses that are applied to the location, the at least one parameter being selected from the group consisting of: a temporal width of the set of electrical stimulation pulses, a frequency of the electrical stimulation pulses, and a current intensity of the electrical stimulation pulses.

12. The apparatus according to claim 11, wherein the computer processor is configured to modulate parameters of further sets of electrical stimulation pulses that are applied to the location by, iteratively, reducing the selected at least one parameter of sets of electrical stimulation pulses that are applied to the location, in response to receiving inputs from the subject that are indicative of the subject having correctly sensed the location at which the sets of electrical stimulation pulses were applied.

13. The apparatus according to claim 1, wherein the computer processor is configured to modulate parameters of the sets of electrical stimulation pulses that are applied to respective locations upon the surface of the body portion by:

in response to receiving an input from the subject that is indicative of the subject having incorrectly sensed the given set of electrical stimulation pulses as having been applied at the location that is different from the location at which the given set of electrical stimulation pulses were applied, increasing the at least one parameter of the further set of electrical stimulation pulses that are applied to the location at which the given set of electrical stimulation pulses were applied, the at least one parameter being selected from the group consisting of: a temporal width of the set of electrical stimulation pulses, a frequency of the electrical stimulation pulses, and a current intensity of the electrical stimulation pulses.

14. The apparatus according to claim 13, wherein the computer processor is configured to modulate parameters of further sets of electrical stimulation pulses that are applied to the location by, iteratively, increasing the selected at least one parameter of further sets of electrical stimulation pulses that are applied to the location at which the set of electrical stimulation pulses were applied, until an input is received from the subject that is indicative of the subject having correctly sensed a given set of electrical stimulation pulses as having been applied at the location.

15. The apparatus according to claim 1, wherein the computer processor is configured to modulate parameters of the sets of electrical stimulation pulses that are applied to respective locations upon the surface of the body portion by:

in response to receiving an input from the subject that is indicative of the subject not having sensed the given set of electrical stimulation pulses as having been applied at the given location, increasing at least one parameter of the further set of electrical stimulation pulses that are applied to the given location, the at least one parameter being selected from the group consisting of: a temporal width of the set of electrical stimulation pulses, a frequency of the electrical stimulation pulses, and a current intensity of the electrical stimulation pulses.

16. The apparatus according to claim 15, wherein the computer processor is configured to modulate parameters of the sets of further sets of electrical stimulation pulses that are applied to respective locations upon the surface of the body portion by, iteratively, increasing the selected at least one parameter of sets of electrical stimulation pulses that are applied to the given location, until an input is received from the subject that is indicative of the subject having correctly sensed a given set of electrical stimulation pulses as having been applied at the given location.

17. The apparatus according to claim 1, further comprising a wearable garment configured to be worn by the subject, wherein the plurality of electrodes are disposed upon the wearable garment and are configured to be placed at the respective locations upon the surface of the body portion by the subject wearing the garment.

18. The apparatus according to claim 17, wherein the garment is selected from the group consisting of: a glove, a sock, a patch, and a cuff.

19. The apparatus according to claim 1,
wherein the user interface is configured to display a graphical representation of the body portion, and
wherein the computer processor is configured to receive each of the inputs indicative of the location at which the subject sensed the set of electrical stimulation pulse as having been applied by receiving an indication from the subject of the location upon the displayed graphical representation of the body portion.

20. A method comprising:
placing a plurality of electrodes at respective locations upon a surface of a portion of a body of a subject; and
increasing sensitivity of sensory nerves of the body portion by activating at least one computer processor to:
apply sets of electrical stimulation pulses to a plurality of locations upon a surface of the body portion, via the electrodes;
receive respective inputs from the subject via a user interface, each of the inputs corresponding to a respective one of the sets of electrical stimulation pulses, and being indicative of a location at which the subject sensed the set of electrical stimulation pulses as having been applied; and
in response to the inputs from the subject and whether the subject (a) correctly sensed a location at which a given set of electrical stimulation pulses were applied or (b) incorrectly sensed that the given set of electrical stimulation pulses were applied at a location different from the location at which the given set of electrical stimulation pulses were applied, modulate at least one parameter of a further set of electrical stimulation pulses that are applied to the location upon the surface of the body portion.

21. The method according to claim 20, wherein activating the at least one computer processor comprises activating the at least one computer processor to:
apply the sets of electrical stimulation pulses to the plurality of locations upon a surface of the body portion by applying, to at least some of the plurality of locations, sets of electrical stimulation pulses that are configured to generate muscle movement within the body portion, and
receive the inputs from the subject by receiving at least some inputs from the subject that are indicative of locations at which the subject sensed the muscle movement.

22. The method according to claim 20, wherein activating the at least one computer processor comprises activating the at least one computer processor to:
further detecting surface electromyography signals from the respective locations upon the surface of the body portion, and
modulate parameters of the sets of electrical stimulation pulses that are applied to respective locations upon the surface of the body portion by modulating parameters of the sets of electrical stimulation pulses that are applied to respective locations upon the surface of the body portion in response to the inputs from the subject and the received surface electromyography signals.

23. The method according to claim 20, wherein activating the at least one computer processor comprises activating the at least one computer processor, in response to the inputs from the subject and whether the subject correctly or incorrectly sensed the location at which the given set of electrical stimulation pulses were applied, to generate an output to the subject, via the user interface, that is indicative of whether the subject correctly sensed the location at which the given set of electrical stimulation pulses were applied.

24. The method according to claim 20, wherein activating the at least one computer processor comprises activating the at least one computer processor to modulate parameters of the sets of electrical stimulation pulses that are applied to respective locations upon the surface of the body portion by modulating parameters of the sets of pulses that are applied at the respective locations, over a course of a treatment session, such that stimulation that is provided at the respective locations moves dynamically toward a sensitivity threshold of the subject.

25. The method according to claim 20, wherein activating the at least one computer processor comprises activating the at least one computer processor to modulate parameters of the sets of electrical stimulation pulses that are applied to respective locations upon the surface of the body portion by:

in response to receiving an input from the subject that is indicative of the subject having correctly sensed the location at which the given set of electrical stimulation pulses were applied, reducing the at least one parameter of the further set of electrical stimulation pulses that are applied to the location, the at least one parameter being selected from the group consisting of: a temporal width of the set of electrical stimulation pulses, a frequency of the electrical stimulation pulses, and a current intensity of the electrical stimulation pulses.

26. The method according to claim 20, wherein activating the at least one computer processor comprises activating the at least one computer processor to modulate parameters of the sets of electrical stimulation pulses that are applied to respective locations upon the surface of the body portion by:

in response to receiving an input from the subject that is indicative of the subject having incorrectly sensed the given set of electrical stimulation pulses as having been applied at the location that is different from the location at which the given set of electrical stimulation pulses was applied, increasing the at least one parameter of the further set of electrical stimulation pulses that are applied to the location at which the given set of electrical stimulation pulses were applied, the at least one parameter being selected from the group consisting of: a temporal width of the set of electrical stimulation pulses, a frequency of the electrical stimulation pulses, and a current intensity of the electrical stimulation pulses.

27. The method according to claim 20, wherein activating the at least one computer processor comprises activating the at least one computer processor to modulate parameters of the sets of electrical stimulation pulses that are applied to respective locations upon the surface of the body portion by:

in response to receiving an input from the subject that is indicative of the subject not having sensed the given set of electrical stimulation pulses as having been applied at the given location, increasing at least one parameter of the further set of electrical stimulation pulses that was applied to the given location, the at least one parameter being selected from the group consisting of: a temporal width of the set of electrical stimulation pulses, a frequency of the electrical stimulation pulses, and a current intensity of the electrical stimulation pulses.

* * * * *